United States Patent [19]

Freitag et al.

[11] Patent Number: 5,210,328

[45] Date of Patent: May 11, 1993

[54] PROCESS FOR THE PREPARATION OF SUBSTITUTED CYCLOALKYLIDENE BISPHENOLS

[75] Inventors: Dieter Freitag; Claus H. Wulff, both of Krefeld; Alfred Eitel, Dormagen; Helmut Waldmann, Leverkusen; Uwe Westeppe, Mettmann; Manfred Hajek, Leverkusen; Klaus D. Berg, Krefeld; Bernd Griehsel, Bottrop; Carl Casser, Köln, all of Fed. Rep. of Germany

[73] Assignee: Bayer Aktiengesellschaft, Leverkusen, Fed. Rep. of Germany

[21] Appl. No.: 904,186

[22] Filed: Jun. 25, 1992

[30] Foreign Application Priority Data

Jul. 2, 1991 [DE] Fed. Rep. of Germany ....... 4121791

[51] Int. Cl.$^5$ .............................................. C07C 39/17
[52] U.S. Cl. .................... 568/721; 568/718; 568/722; 568/728; 526/196
[58] Field of Search ............... 568/721, 722, 727, 728; 526/196

[56] References Cited

U.S. PATENT DOCUMENTS

| | | | |
|---|---|---|---|
| 2,069,560 | 2/1937 | Rothrock | 568/721 |
| 2,069,573 | 2/1937 | Bolton | 568/721 |
| 2,883,365 | 4/1959 | Mark | 568/721 |
| 3,491,157 | 1/1970 | Deitzler et al. | 568/721 |
| 4,387,251 | 6/1983 | Meyer et al. | 568/727 |
| 4,912,263 | 3/1990 | Rudolph et al. | 568/722 |
| 4,982,014 | 1/1991 | Frietag et al. | 568/721 |
| 5,126,428 | 6/1992 | Freitag et al. | 568/721 |

FOREIGN PATENT DOCUMENTS

| | | |
|---|---|---|
| 0026318 | 4/1981 | European Pat. Off. . |
| 0305774 | 3/1989 | European Pat. Off. . |
| 0328085 | 8/1989 | European Pat. Off. . |
| 0359953 | 3/1990 | European Pat. Off. . |
| 3832396 | 2/1990 | Fed. Rep. of Germany ...... 568/721 |

OTHER PUBLICATIONS

Derwent Database, JP 57 031 629.

*Primary Examiner*—Werren B. Lone
*Attorney, Agent, or Firm*—Connolly & Hutz

[57] ABSTRACT

This invention relates to a process for the preparation of substituted cycloalkylidene bisphenols from phenols and special cycloalkanones in the presence of acid condensation catalysts and in the presence of water.

2 Claims, No Drawings

PROCESS FOR THE PREPARATION OF SUBSTITUTED CYCLOALKYLIDENE BISPHENOLS

This invention relates to a process for the preparation of substituted cycloalkylidene bisphenols from phenols and special cycloalkanones in the presence of acid condensation catalysts and in the presence of water.

The cycloalkylidene bisphenols prepared according to the invention are valuable intermediate products for the preparation of polycondensation products. In particular, they are suitable for the preparation of polyether ketones, polyether sulphones and polycarbonates which are distinguished by their high glass temperature, exceptionally good mould release properties and exceptionally good melt flow capacity, especially in view of the high glass temperature, and very good stability against UV, heat and hydrolysis.

The preparation of cyclohexylidene bisphenols corresponding to formula (I)

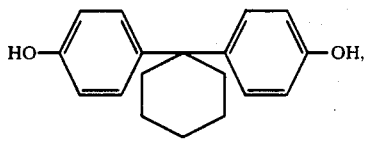

wherein
R denotes a $C_1$–$C_{12}$ hydrocarbon group and
n stands for the number 0, 1 or 2
but with the exclusion of geminal disubstitution
from phenol and special cyclohexanones in the presence of sulphonic acids or acid ion exchangers as condensation catalysts and optionally in the presence of mercapto compounds as cocatalysts is already known (e.g. DE-A 29 35 316). The anhydrous use of the condensing agents and the continuous removal of the water of reaction formed are particularly mentioned.

It was found that geminally disubstituted cycloalkanones can be reacted highly selectively with phenols in the presence of sulphonic acids, hydrogen chloride or acid ion exchangers as condensation catalysts and optionally in the presence of mercapto compounds as cocatalysts to produce the corresponding bisphenols if water is added to the reaction mixture.

The invention relates to a process for the preparation of substituted cycloalkylidene bisphenols corresponding to formula (II)

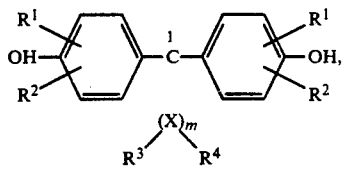

wherein
$R^1$ and $R^2$ denote, independently of one another, hydrogen, halogen, preferably chlorine or bromine, $C_1$–$C_8$-alkyl, $C_5$–$C_6$-cycloalkyl, $C_6$–$C_{10}$-aryl, preferably phenyl, and $C_7$–$C_{12}$-aralkyl, preferably phenyl-$C_1$–$C_4$-alkyl, in particular benzyl,
m stands for an integer from 4 to 7, preferably 4 or 5,
$R^3$ and $R^4$, which can be chosen individually for each X, denote, independently of one another, hydrogen, straight chain or branched $C$–$C_6$-alkyl, $C_6$–$C_{10}$-aryl, preferably phenyl, and $C_7$–$C_{12}$-aralkyl, preferably phenyl-$C_1$–$C_4$-alkyl, and
X denotes carbon
under the condition that on at least one X atom, the $R^3$ and $R^4$ are not both hydrogen
by the reaction of phenols corresponding to formula (III)

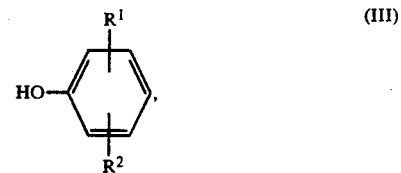

wherein
$R^1$ and $R^2$ have the meanings indicated for formula (II)
with ketones corresponding to formula (IV)

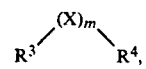

in which $R^3$, $R^4$, X and m have the meanings indicated for formula (II)
in the presence of acid condensation catalysts and optionally in the presence of organic sulphur compounds as cocatalyst, characterised in that water is added to the reaction mixture.

Those cycloalkylidene bisphenols of formula (II) are preferred in which $R^3$ and $R^4$ both stand for alkyl on one or two X atoms, in particular on only one X atom. Methyl is the preferred alkyl group. The X atoms in the 2-position to the di-4-hydroxyphenyl-substituted carbon atom (C-1) are preferably substituted by hydrogen, and alkyldisubstitution is preferred in the $\beta$-position to C-1. Dialkyl substitution of one X atom in the $\beta$-position and monoalkyl substitution of one X atom in the $\beta$-position is particularly preferred.

The bisphenols of formulae (V) to (IX), for example, may be prepared:

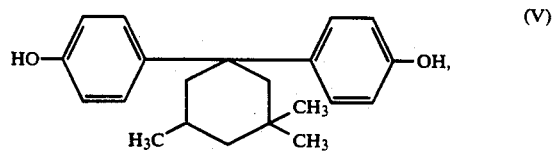

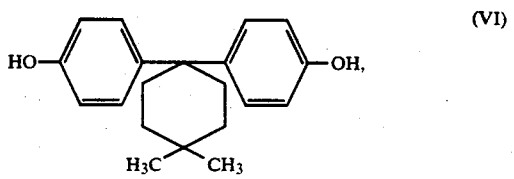

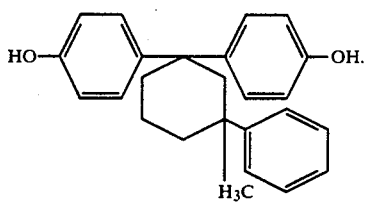
(VII)

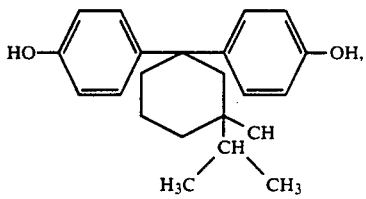
(VIII)

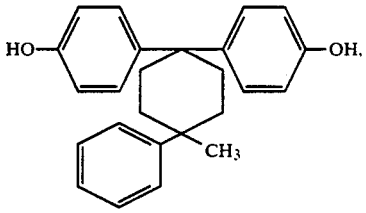
(IX)

1,1-Bis-(4-hydroxyphenyl)-3,3,5-trimethylcyclohexane (formula V) is preferred.

The following are examples of suitable phenols corresponding to formula (III): Phenol, o-cresol, m-cresol, 2,6-dimethylphenol, 2-chlorophenol, 3-chlorophenol, 2,6-dichlorophenol, 2-cyclohexylphenol, 2,6-diphenylphenol and o-benzylphenol.

The following are examples of suitable cycloalkanones corresponding to formula (IV): 3,3,5-Trimethylcyclohexanone, 3,3-dimethylcyclohexanone, 4-methyl-4-phenylcyclohexanone, 3-methyl-3-isopropylcyclohexanone, 4,4-diphenylcyclohexanone, 4-methyl-4-phenylcyclohexanone and 3,3-dimethyl-5-phenylcyclohexanone.

In the process according to the invention, the phenol of formula (III) is used ,in stoichiometric excess over the cycloalkanones of formula (IV). From 3 to 35 mol of phenol are preferably used per mol of ketone. A molar ratio of phenol to cycloalkanone in the range of from 3:1 to 30:1 is particularly preferred.

Aromatic and aliphatic sulphonic acids are suitable acid condensation catalysts for the process according to the invention. Mono- and polysulphonic acids corresponding to the general formulae (X) and (XI) are preferred:

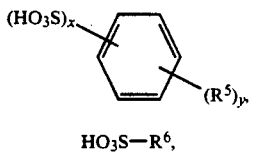

(X)

$HO_3S-R^6$, (XI)

wherein $R^5$, which can be freely chosen for each y, denotes hydrogen, halogen, preferably chlorine or bromine, $C_1-C_{12}$ straight chain or branched alkyl, $C_5-C_6$ cycloalkyl, $C_6-C_{10}$-aryl, $C_7-C_{12}$-aralkyl, OH, SH, $OR^7$, $SR^7$, $SO_2R^7$, $NO_2$ and COOH, $R^6$ denotes $C_1-C_{12}$ straight chain or branched alkyl, $C_5-C_6$-cycloalkyl and $C_7-C_{12}$-aralkyl, $R^7$ denotes an aliphatic or aromatic hydrocarbon group which may carry inert substituents and x and y denote, independently of one another, an integer from 1 to 5, under the condition that the sum of x and y amounts to 6.

Examples of suitable sulphonic acids corresponding to formulae (X) and (XI) include benzene sulphonic acid, 4-hydroxyphenyl sulphonic acid, 4-dodecylphenyl sulphonic acid, 2-methoxyphenyl sulphonic acid and methane sulphonic acid.

These sulphonic acids may be used over a wide range as acid condensation catalysts for the preparation of bisphenol, preferably in quantities of from 0.1 to 2 mol per mol of cycloalkanone corresponding to formula (IV).

Hydrogen chloride, sulphonated styrene-divinylbenzene resins, sulphonated cross-linked styrene polymers or phenol-formaldehyde sulphonic acid resins may be used as acid condensation catalysts in the process according to the invention instead of the sulphonic acids of formulae (X) and (XI). These alternative acid condensation catalysts are obtainable under the names of Amberlite®, DOWEX®, Permutit QH®, Chempro® and Lewatite®. Polyperfluoroalkylene sulphonic acids obtainable under the name of Nafion® may also be used.

The ion exchangers used have a H+ ion capacity of from 2 to 7 mval/g of dry substance.

The reaction velocity may be increased by the addition of known sulphur-containing cocatalysts. When sulphonic acids or hydrogen chloride are used as condensation catalysts, these cocatalysts are added to the reaction mixture in the form of low molecular weight compounds, e.g. as β-mercaptopropionic acid or n-alkylmercaptan. The cocatalyst is used in quantities of from 0.001 to 0.3 mol per mol of cycloalkanone of (IV). When acid ion exchangers are used as condensation catalysts, the mercapto-containing cocatalyst may also be fixed to the ion exchanger, either directly to the matrix or by way of the sulphonic acid groups. Such modifications of acid ion exchangers are known (see EP-A 305 774, EP-A 023 325 and DE-A 2 722 683).

The reaction temperature in the process according to the invention is from 20° to 150° C. Temperatures from 30° to 90° C. are preferred. Pressures of from 1 to 20 bar are generally employed, preferably from 1 to 10 bar.

In the process according to the invention, water is added to the reaction mixture to increase the selectivity. The quantity of water added may vary within wide limits and is preferably from 700 to 20 mol of water per 100 kg of reaction mixture of phenols, cyclohexanones, cocatalysts, condensation catalysts and water. The quantity of water used depends on the acid concentration present, e.g. a high concentration of water is an advantage at high acid concentrations.

Since the reaction velocity decreases with increasing water content and 1 mol of water of reaction is formed per mol of bisphenol, it is advantageous to keep the water content constant, especially in a continuous process, for example by vacuum distillation, azeotropic distillation of solvent-water mixtures, etc..

The process according to the invention may be carried out continuously or batchwise and the reaction may also be carried out in an inert solvent (see also DE-A 29 35 316).

EXAMPLES

Example 1

To ascertain the influence of the quantity of water on the selectivity of the bisphenol formed, distilled benzene sulphonic acid (0.4 mol) were added at 30° C. to a mixture of 6 mol of phenol, 0.97 mol of 3,3,5-trimethylcyclohexanone, 0.13 mol of β-mercaptopropionic acid and water (for quantity see Table 1), in several parallel reaction mixtures. The reaction mixtures were stirred at 30° to 35° C. The selectivity and degree of conversion were determined gas chromatographically.

TABLE 1

| Experiment | $H_2O$ content [mol/100 kg] | Conversion [%] | Selectivity [%] |
|---|---|---|---|
| 1 | 174 | 60 | 80 |
| 2 | 88 | 60 | 65 |
| 3 | 45 | 60 | 61 |
| 4 | 22 | 60 | 54 |
| 5 | — | 60 | 46 |
| 5 | — | 90 | 65 |
| 2 | 88 | 90 | 80 |
| 3 | 45 | 90 | 75 |
| 4 | 22 | 90 | 70 |

EXAMPLE 2

This was carried out analogously to Example 1 but using 0.4 mol of methane sulphonic acid instead of 0.4 mol of benzene sulphonic acid. The results are summarized in Table 2.

TABLE 2

| Experiment | $H_2O$ content [mol/100 kg] | Conversion rate [%] | Selectivity [%] |
|---|---|---|---|
| 6 | 179 | 70 | 81 |
| 7 | 91 | 70 | 70 |
| 8 | 46 | 70 | 65 |
| 9 | 23 | 70 | 60 |
| 6 | 179 | 90 | 85 |
| 9 | 23 | 90 | 69 |

EXAMPLE 3

Comparison Example

Analogous to Example 2 but with the 0.97 mol of 3,3,5-trimethylcyclohexanone replaced by 0.97 mol of 4-tert.-butylcyclohexanone. The results are summarized in Table 3.

| Experiment | $H_2O$ content [mol/100 kg] | Conversion rate [%] | Selectivity [%] |
|---|---|---|---|
| 10 | 178 | 90 | 93 |
| 11 | 23 | 90 | 92 |

EXAMPLE 4

Carried out analogously to Example 1; phenol and 3,3,5-trimethylcyclohexanone were reacted in a molar ratio of 6 to 1 in a stirrer apparatus at 30° C. at a β-mercaptopropionic acid concentration of 0.16 mol/kg and an HCl concentration of 0.49 mol/kg in the presence of water. The dependence of the selectivity on the $H_2O$ concentration is shown in Table 4.

TABLE 4

| Experiment | $H_2O$ content [mol/100 kg] | Conversion rate [%] | Selectivity [%] |
|---|---|---|---|
| 12 | 44.4 | 95 | 85 |
| 13 | 89.3 | 95 | 91 |

EXAMPLE 5

Experiments were carried out analogously to Example 4, using a β-mercaptopropionic acid concentration of 0.24 mol/kg. The results are summarized in Table 5.

TABLE 5

| Experiment | $H_2O$ content [mol/100 kg] | Conversion rate [%] | Selectivity [%] |
|---|---|---|---|
| 14 | 44.4 | 95 | 86 |
| 15 | 89.3 | 95 | 92 |

EXAMPLE 6

A vertically arranged glass column 1 meter in length and 8 cm in internal diameter was filled with 400 g of washed and dried cation exchanger resin (Lewatit SC 102/H ®). A mixture of 30 mol of phenol, 1 mol of 3,3,5-trimethylcyclohexanone and 0.15 mol of β-mercaptopropionic acid was continuously pumped through this glass column at 40° to 45° C. and at a rate of 100 g/h.

The selectivity of 1,1-bis-(4-hydroxyphenyl)-3,3,5-trimethylcyclohexane was 55%. When water was added to the reaction mixture ($H_2O$ content: 28 mol/100 kg), the selectivity was 72%.

We claim:

1. A process for the preparation of substituted cycloalkylidene bisphenols corresponding to formula (II)

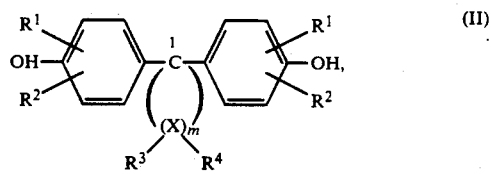

wherein $R^1$ and $R^2$ denote, independently of one another, hydrogen, halogen, $C_1$–$C_8$-alkyl, $C_5$–$C_6$-cycloalkyl, $C_6$–$C_{10}$-aryl and $C_7$–$C_{12}$-aralkyl, m stands for an integer from 4 to 7, $R^3$ and $R^4$ which may be chosen individually for each X, denote, independently of one another, hydrogen, straight chain or branched $C_1$–$C_6$-alkyl, $C_6$–$C_{10}$-aryl and $C_7$–$C_{12}$-aralkyl and X denotes carbon under the condition that on at least one X atom, $R^3$ and $R^4$ are not both hydrogen, by the reaction of phenols corresponding to the formula (III)

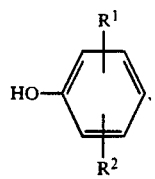
(III)

in which $R^1$ and $R^2$ have the meanings given for formula (II)

with ketones corresponding to formula (IV)

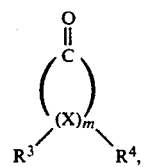
(IV)

in which $R^3$, $R^4$, X and m have the meanings indicated for formula (II) in the presence of acid condensation catalysts, wherein the reaction is carried out in the presence of 20 to 700 mol of water per 100 kg of reaction mixture, at a temperature of 20° to 150° C., at a pressure of 1 to 20 bar.

2. The process of claim 1 wherein an organic sulfur compound is present as cocatalyst.

* * * * *